ABSTRACT

Essential fatty acids are rendered oxidationstable by mixture with jojoba oil to form a solution.

4 Claims, No Drawings

SOLUTIONS CONTAINING AT LEAST ONE ESSENTIAL FATTY ACID AND VEGETABLE OIL, AND COSMETIC COMPOSITIONS CONTAINING THESE SOLUTIONS

DESCRIPTION

The present invention relates to a solution, which is stable to oxidation, of at least one essential fatty acid, in particular vitamin F, and of a vegetable oil, and also to various cosmetic compositions in which a solution of this type is present.

The cosmetic use of vitamins for topical application has been recommended by numerous authors.

Amongst the vitamins more particularly recommended, there may be mentioned vitamin A, vitamin B, vitamins B2 and B6, vitamin E, vitamin F and also certain mixtures of vitamins, such as a mixture of vitamins A, E and D3, the association of which has been shown to exhibit a synergistic effect.

Amongst these vitamins, the one which has more particularly held the attention of cosmeticians is vitamin F, which essentially consists of a mixture of essential fatty acids (EFA). In fact, this vitamin has been shown to possess certain properties which are particularly sought after for improving the appearance of the skin.

Vitamin F in fact exerts a beneficial action on skin exhibiting dryness or roughness and also on skin exhibiting signs of irritation.

However, the cosmetic use of vitamin F has come up against a particularly acute difficulty essentially due to its high instability to oxidation by the oxygen in the atmosphere. In fact, it has been found that decomposition products with a rancid odour form very rapidly after the first use, thus excluding any subsequent use of cosmetic compositions based on this vitamin.

Since vitamin F consists essentially of linoleic acid and partially of linolenic acid, and of their isomers and other acids which are very sensitive to oxidation, the corresponding alcohols, which are more stable, or the esters of these acids, have been used but this results in a very substantial reduction in activity.

In an attempt to overcome these various disadvantages and to obtain compositions of high stability to atmospheric oxidation, it has been found, surprisingly, according to the present invention, that this result can be achieved if the essential fatty acids, in particular vitamin F are used in association with a particular vegetable oil, namely jojoba oil.

In fact, experiments which we have carried out make it possible to show that the associations of at least one essential fatty acid, or mixtures of fatty acids, in particular vitamin F, and of jojoba oil possess a remarkable stability to oxidation, which stability is not present with other vegetable oils, such as sunflower seed oil.

The present invention accordingly provides a solution, which is stable to oxidation, of at least one essential fatty acid, or a mixture of essential fatty acids, and of a vegetable oil, the said oil being jojoba oil.

The expression "essential fatty acid" is to be understood as meaning an unsaturated fatty acid possessing at least two double bonds, such as:

1. linoleic acid or 9,12-octadecadienoic acid of the formula:

$$CH_{13}(CH_2)_4—CH=CH—CH_2—CH=CH—(CH_2)_7—COOH$$

and its stereoisomers, in particular the Z-9, Z-12 isomer, and also its position isomers, or conjugated linoleic acids; namely:

(i) 9,11-octadecadienoic acid of the formula:

$$CH_3—(CH_2)_5—CH=CH—CH=CH—(CH_2)_7—COOH$$

and its stereoisomers, or (ii) 10,12-octadecadienoic acid of the formula:

$$CH_3—(CH_2)_4—CH=CH—CH=CH—(CH_2)_8—COOH$$

and its stereoisomers;

2. α-linolenic or 9,12,15-octadecatrienoic acid of the formula:

$$CH_3—(CH_2—CH=CH)_3—CH_2—(CH_2)_6—COOH$$

and its stereoisomers, in particular the Z-9, Z-12, Z-15 isomer;

3. γ-linolenic or 6,9,12-octadecatrienoic acid of the formula:

$$CH_3—(CH_2)_3—(CH_2—CH=CH)_3—CH_2—(CH_2)_3—COOH$$

and its stereoisomers; and 4. arachidonic acid or 5,8,11,14-eicosatetraenoic acid of the formula:

$$CH_3—(CH_2)_4—(CH=CH—CH_2)_4—CH_2—CH_2—COOH$$

and its stereoisomers.

As indicated above, vitamin F essentially consists of linoleic acid and its isomers, the 9,12 isomer being present in a proportion generally from 40 to 70%, the total proportion of the linoleic acids (linoleic acid + isomers) generally representing from 80 to 90%, the remainder essentially consisting of a mixture of other essential fatty acids.

Jojoba oil is a vegetable oil extracted from *Simmondsia chinensis*; it possesses the following characteristics:

viscosity: (Brookfield 25° C.) about 37 cp.
colour: light yellow to colourless (purified)
density at 25° C.: about 0.863
iodine number: 80–82
n$_D$25° C.=1.4645–1.4650

According to the invention, the jojoba oil typically represents from 99.5 to 80% by weight of the total weight of the solution, so that the concentration of essential fatty acid(s) or of a mixture of essential fatty acids is from 0.5 to 20% by weight.

Concentrations of more than 20% of at least one essential fatty acid in the jojoba oil can however be envisaged without materially detracting from the stability to oxidation. In fact, it has been found, surprisingly and contrary to all expectation, that the stability tends to improve as a function of the increase in the concentration of essential fatty acid(s); the opposite effect would have been expected.

However, for practical reasons, and in particular because of the purpose for which the solutions according to the invention are intended, the concentration of essential fatty acid(s) is not generally more than 20% by weight.

The present invention also provides cosmetic compositions containing a solution which is stable to oxidation, as defined above.

These cosmetic compositions can generally be any composition containing one or more oils. Amongst these compositions, there may be mentioned, in particular, those which are presented in the form of fluid emulsions (milks), in the form of lotions or in the form of emulsions of greater consistency (creams).

The compositions are, for example, emollient milks or creams, milks or creams for hand care, make-up removal creams or milks, make-up foundations, "anti-sunburn" milks or creams, milks or creams for artificial tanning, antiperspirant milks or creams and shaving creams or foams.

These cosmetic compositions can also be presented in the form of sticks for the lips, which are intended either to colour them or to prevent cracking, eye make-up products or rouges.

According to the invention, the solution of this invention suitably represents from 5 to 99% by weight of the total weight of the composition.

If the cosmetic compositions according to the present invention essentially consist of the solution which is stable to oxidation, they are, in particular, anti-sunburn oils (containing a sun filter which absorbs ultraviolet), hand oils, body oils, pre-shave or aftershave oils or bath oils.

The compositions according to the invention generally contain other ingredients, in particular preservatives, perfumes or colouring agents.

By virtue of the good stability of the stable solution according to the invention, it is not necessary to use antioxidants.

In this respect, it has been found that the compositions according to the invention are particularly stable even if they contain a pre-oxidant, such as $\alpha$-tocopherol or vitamin E.

If the compositions are presented in the form of emulsions of the water-in-oil or oil-in-water type, the oil phase can essentially consist of the stable solution based on jojoba oil, but preferably based on a mixture with at least one other oil which cannot grow rancid, and, if appropriate, on at least one wax.

The oil phase of the emulsions is suitably from 5 to 60% by weight, relative to the total weight of the emulsion.

The water phase of the said emulsions is preferably from 30 to 85%, relative to the total weight of the emulsion.

The proportions of the emulsifier is suitably 1 to 20% and preferably 2 to 12%, by weight.

The emulsions according to the invention can also contain so-called filler substances, such as titanium oxide, zinc oxide, talc or kaolin, and also colouring substances, in particular iron oxides, such as red iron oxide, yellow iron oxide and black iron oxide.

The following Examples further illustrate the present invention.

EXAMPLE 1

| | |
|---|---|
| 9,12-Octadecadienoic acid | 15 g |
| Jojoba oil | 85 g |

EXAMPLE 2

| | |
|---|---|
| 9,11-Octadecadienoic acid | 10 g |
| Jojoba oil | 90 g |

EXAMPLE 3

| | |
|---|---|
| 10,12-Octadecadienoic acid | 12 g |
| Jojoba oil | 88 g |

EXAMPLE 4

| | |
|---|---|
| 9,12,15-Octadecatrienoic acid | 10 g |
| Jojoba oil | 90 g |

EXAMPLE 5

| | |
|---|---|
| 6,9,12-Octadecatrienoic acid | 15 g |
| Jojoba oil | 85 g |

EXAMPLE 6

| | |
|---|---|
| 5,8,11,14-Eicosatetraenoic acid | 8 g |
| Jojoba oil | 92 g |

EXAMPLE 7

| | |
|---|---|
| 9,12-Octadecadienoic acid | 7 g |
| 6,9,12-Octadecatrienoic acid | 5 g |
| 5,8,11,14-Eicosatetraenoic acid | 3 g |
| Jojoba oil | 85 g |

EXAMPLE 8

| | |
|---|---|
| 5,8,11,14-Eicosatetraenoic acid | 5 g |
| 9,12,15-Octadecatrienoic acid | 8 g |
| Jojoba oil | 87 g |

EXAMPLE 9

| | |
|---|---|
| 9,12-Octadecadienoic acid | 5 g |
| 9,11-Octadecadienoic acid | 4 g |
| 5,8,11,14-Eicosatetraenoic acid | 2 g |
| Jojoba oil | 89 g |

EXAMPLE I

A sun oil is prepared according to the invention by mixing the following ingredients:

| | |
|---|---|
| Solution according to Example 5 | 95 g |
| Sun filter "PARSOL ULTRA" sold by the Societe GIVAUDAN | 5 g |

EXAMPLE II

A care cream in the form of a water-in-oil emulsion is prepared according to the invention by mixing the following ingredients:

| | |
|---|---|
| Aluminium lanolate | 10 g |
| Lanolin alcohol | 40 g |
| Solution according to Example 10 | 8 g |
| Ozokerite | 2 g |
| Perfume | 0.1 g |
| Methyl p-hydroxybenzoate | 0.1 g |
| Water q.s.p. | 100 g |

EXAMPLE III

A sun cream in the form of a water-in-oil emulsion is prepared according to the invention by mixing the following ingredients:

| | |
|---|---|
| 2-Dimethylaminoethyl methacrylate/lauryl methacrylate block copolymer ($\overline{Mw}$ = 8,000) | 6 g |
| Solution according to Example 6 | 35.6 g |
| Microcrystalline wax | 2 g |
| Sun filter "PARSOL ULTRA" | 5 g |
| Perfume | 0.2 g |
| Water q.s.p. | 100 g |

EXAMPLE IV

A make-up foundation in the form of a water-in-oil emulsion is prepared according to the invention by mixing the following ingredients:

| | |
|---|---|
| 2-Vinylpyridine/lauryl methacrylate block copolymer ($\overline{Mw}$ = 110,000) | 7.4 g |
| Solution according to Example 4 | 44 g |
| Titanium oxide | 1.5 g |
| Ochre colorant | 1.5 g |
| Perfume | 0.15 g |
| Lactic acid | 3.4 g |
| Water q.s.p. | 100 g |

EXAMPLE V

A care cream in the form of an oil-in-water emulsion is prepared according to the invention by mixing the following ingredients:

| | |
|---|---|
| Lanolic acid | 7 g |
| Histidine | 3 g |
| Solution according to Example 8 | 30 g |
| Water q.s.p. | 100 g |

EXAMPLE VI

A make-up removal milk is prepared according to the invention by mixing the following ingredients:

| | |
|---|---|
| Solution according to Example 7 | 15 g |
| Glycerol stearate | 2 g |
| Stearic acid | 1.4 g |
| Carbopol 934 (crosslinked polyacrylic acid sold by the Societe Goodrich) | 0.6 g |
| Triethanolamine | 1.3 g |
| Methyl p-hydroxybenzoate | 0.25 g |
| Perfume | 0.1 g |
| Water q.s.p. | 100 g |

EXAMPLE VII

A body oil is prepared according to the invention by mixing the following ingredients:

| | |
|---|---|
| Vitamin F | 15 g |
| Jojoba oil | 85 g |

EXAMPLE VIII

A sun oil is prepared according to the invention by mixing the following ingredients:

| | |
|---|---|
| 15% strength solution of vitamin F in jojoba oil | 95 g |
| Sun filter "PARSOL ULTRA" | 5 g |

EXAMPLE IX

A care cream in the form of a water-in-oil emulsion is prepared according to the invention by mixing the following ingredients:

| | |
|---|---|
| Aluminium lanolate | 10 g |
| Lanolin alcohol | 40 g |
| 10% strength solution of vitamin F in jojoba oil | 8 g |
| Ozokerite | 2 g |
| Perfume | 0.1 g |
| Methyl para-hydroxybenzoate | 0.1 g |
| Water q.s.p. | 100 g |

EXAMPLE X

A sun cream in the form of a water-in-oil emulsion is prepared according to the invention by mixing the following ingredients:

| | |
|---|---|
| 2-Dimethylaminoethyl methacrylate/lauryl methacrylate block copolymer ($\overline{Mw}$ = 8,000) | 6 g |
| 7.8% strength solution of vitamin F in jojoba oil | 35.6 g |
| Microcrystalline wax | 2 g |
| Sun filter "PARSOL ULTRA" | 5 g |
| Perfume | 0.2 g |
| Sterile demineralised water q.s.p. | 100 g |

EXAMPLE XI

A make-up foundation in the form of a water-in-oil emulsion is prepared according to the invention by mixing the following ingredients:

| | |
|---|---|
| 2-Vinylpyridine/lauryl methacrylate block copolymer ($\overline{Mw}$ = 110,000) | 7.4 g |
| 9.3% strength solution of vitamin F in jojoba oil | 44 g |
| Titanium oxide | 1.5 g |
| Ochre colorant | 1.5 g |
| Perfume | 0.15 g |
| Lactic acid | 3.4 g |
| Sterile demineralised water q.s.p. | 100 g |

EXAMPLE XII

A care cream in the form of an oil-in-water emulsion is prepared according to the invention by mixing the following ingredients:

| | |
|---|---|
| Lanolic acid | 7 g |
| Histidine | 3 g |
| 10% strength solution of vitamin F in jojoba oil | 30 g |
| Sterile demineralised water q.s.p. | 100 g |

EXAMPLE XIII

A make-up removal milk is prepared according to the invention by mixing the following ingredients:

| | |
|---|---|
| 6.6% strength solution of vitamin F in jojoba oil | 15 g |
| Glycerol stearate | 2 g |
| Stearic acid | 1.4 g |
| Carbopol 934 (crosslinked polyacrylic acid sold by the Societe GOODRICH) | 0.6 g |
| Triethanolamine | 1.3 g |
| Methyl para-hydroxybenzoate | 0.25 g |
| Perfume | 0.1 g |
| Sterile demineralised water q.s.p. | 100 g |

EXAMPLE XIV

A make-up foundation in the form of an oil-in-water emulsion is prepared according to the invention by mixing the following ingredients:

| | |
|---|---|
| Lanolic acid | 7.5 g |
| Arginine | 2.5 g |
| 6.6% strength solution of vitamin F in jojoba oil | 30 g |
| Propyl para-hydroxybenzoate | 0.1 g |
| Perfume | 0.2 g |
| Colorants and pigments | 10 g |
| Sterile demineralised water q.s.p. | 100 g |

All the preservation tests carried out on the one hand at ambient temperature (20° C.) and on the other hand at a temperature of 40° C. made it possible to show the excellent stability with time of the solutions and compositions described above.

We claim:

1. A cosmetic composition which comprises an oxidation-stable solution of 0.5 to 20% of an essential fatty acid or a mixture of essential fatty acids in a vegetable oil, said essential fatty acid or acids being selected from the group consisting of linoleic acid or an isomer thereof, a conjugated linoleic acid or an isomer thereof, α-linolenic acid or an isomer thereof, γ-linolenic acid or an isomer thereof, and arachidonic acid or an isomer thereof, and said vegetable oil being jojoba oil in an amount of about 80% to about 99.5% by weight of said solution.

2. The cosmetic composition of claim 1 in which a mixture of essential fatty acids is present, said mixture being vitamin F.

3. An oxidation-stable solution of vitamin F and jojoba oil, said vitamin F being present in an amount of about 0.5 to about 20% by weight, said jojoba oil being present in an amount of about 80% to 99.5% by weight of said solution.

4. A cosmetic water-in-oil or oil-in-water emulsion in which the water phase represents 30 to 85 weight percent of the emulsion, the oil phase represents 5 to 60 weight percent of the emulsion and the emulsifier represents 1 to 20 weight percent of the emulsion, said oil phase consisting essentially of an oxidation-stable solution of an essential fatty acid or a mixture of essential fatty acids in a vegetable oil, said essential fatty acid or acids being selected from the group consisting of linolenic acid or an isomer thereof, a conjugated linoleic acid or an isomer thereof, α-linolenic acid or an isomer thereof, γ-linolenic acid or an isomer thereof, said arachidonic acid or an isomer thereof, said fatty acid or acids being present in an amount of about 0.5 to about 20 weight % of said solution and said vegetable oil being jojoba oil in an amount of about 80% to about 99.5% by weight of said solution and the balance cosmetic ingredients.

* * * * *